(12) United States Patent
Zimmermann et al.

(10) Patent No.: US 7,435,582 B2
(45) Date of Patent: Oct. 14, 2008

(54) SAMPLE CARRIER FOR CRYOCONSERVATION OF BIOLOGICAL SAMPLES

(75) Inventors: Ulrich Zimmermann, Waldbrunn (DE); Heiko Zimmermann, Saarbrucken (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 586 days.

(21) Appl. No.: 10/503,371

(22) PCT Filed: Jan. 29, 2003

(86) PCT No.: PCT/EP03/00902

§ 371 (c)(1),
(2), (4) Date: Oct. 12, 2004

(87) PCT Pub. No.: WO03/065014

PCT Pub. Date: Aug. 7, 2003

(65) Prior Publication Data

US 2005/0037329 A1 Feb. 17, 2005

(30) Foreign Application Priority Data

Jan. 30, 2002 (DE) ............................ 102 03 630

(51) Int. Cl.
*C12M 1/00* (2006.01)
(52) U.S. Cl. .................................................. 435/307.1
(58) Field of Classification Search ............... 435/307.1
See application file for complete search history.

(56) References Cited

U.S. PATENT DOCUMENTS 4,018,911 A 4/1977 Lionetti et al.
4,865,871 A 9/1989 Livesey et al.
5,026,342 A 6/1991 Hammerstedt et al.
5,190,880 A 3/1993 Cassou et al.
5,261,870 A 11/1993 Hammerstedt et al.
5,587,228 A * 12/1996 Baker et al. ................ 428/34.5
5,888,393 A * 3/1999 Luhman et al. ........... 210/510.1
5,986,169 A 11/1999 Gjunter
2001/0030040 A1* 10/2001 Xiao ........................... 165/154
2002/0108957 A1 8/2002 Studer

FOREIGN PATENT DOCUMENTS

DE 197 20 930 A1 11/1997
DE 200 13 334 U1 10/2000
EP 0 853 238 B1 7/1998
EP 0 950 432 A1 10/1999

(Continued)

OTHER PUBLICATIONS

Seiichi, EPO Patent Abstracts of Japan, JP 2001033053 (Feb. 9, 2001).

(Continued)

*Primary Examiner*—Walter D. Griffin
*Assistant Examiner*—Lydia Edwards
(74) *Attorney, Agent, or Firm*—Caesar, Rivise, Bernstein, Cohen & Pokotilow, Ltd.

(57) ABSTRACT

The invention relates to sample supports and methods for cryoconservation, especially the cryoconservation of biological materials, comprising at least one sample reservoir used to receive a biological sample. A support body is disposed in the sample reservoir, made of a material having a volume structure, consisting of a plurality of open, inner cavities which can be filled with the sample. The invention also relates to the use of motor vehicle catalyst-structure or biomorphic ceramics for producing support bodies used to receive samples for cryoconservation.

11 Claims, 2 Drawing Sheets

FOREIGN PATENT DOCUMENTS

| WO | WO 96/02801 A1 | 2/1996 |
| WO | WO 96/21351 A2 | 7/1996 |
| WO | WO 98/20353 A1 | 5/1998 |
| WO | WO 00/24437 A2 | 5/2000 |

OTHER PUBLICATIONS

Toshimitsu, EPO Patent Abstracts of Japan, JP 11093643 (Apr. 6, 1999).

Baust, "A Molecular Basis of Crypreservation Failure and its Modulation to Improve Cell Survival," *Cell Transplantation*, vol. 10, pp. 501-571 (2001).

Eriksson, "Effect of freezing and thawing rates on the post-thaw viability of boar spermatozoa frozen in FlatPacks and Maxi-straw," *Animal Reproduction Science* 63, pp. 205-220 (2000).

Greil, "Biomorphous ceramics from lignocellulosics," *Journal of the European Ceramic Society*, 21, pp. 105-118 (2001).

Miyamoto, "Development of a Cryopreservation Procedure Employing a Freezer Bag for Pancreatic Islets using a Newly Developed Cryoprotectant," *Cell Transplantation*, vol. 10, pp. 363-371 (2001).

Murthy, "Some Insight into the Physical Basis of the Cryoprotective Action of Dimethyl Sulfoxide and Ethylene Glycol," *Cryobiology*, 36, pp. 84-96 (1998).

Park et al., "Ultra-rapid freezing of human multipronuclear zygotes using electron microscope grids," *Human Reproduction*, vol. 15, No. 8, pp. 1787-1790 (2000).

* cited by examiner

SAMPLE CARRIER FOR CRYOCONSERVATION OF BIOLOGICAL SAMPLES

BACKGROUND OF THE INVENTION

The invention relates to sample carriers and methods for cryopreservation of biological samples.

In modern biomedicine and biotechnology there is a continually growing need for cryopreserved biological materials, especially cells, cell groups, natural or artificial tissue, whole organs and cells of embryonic organisms. Cryopreservation is understood as the cooling of biological materials to low, so-called cryogenic temperatures, especially in the range from −80° C. to −196° C. Under these conditions, the metabolism of living cells comes almost to a standstill so that the cells can be stored over many years.

In order to preserve the vitality of cryopreserved cells, special cryomedia are used, comprising protective substances (cryoprotectants) such as dimethyl sulphoxide (DMSO), ethylene glycol, glycerol and sugars such as trehalose or glucose, for example. Cryoprotectants protect the cells by stabilising the cell membranes and macromolecules and by inhibiting intracellular ice formation. The intracellular ice crystals are primarily responsible for irreversible mechanical damage to the cell membranes (see S. S. N. Murthy in "Cryobiology", vol. 36, 1998, p. 84-96). The optimal composition of the cryomedium is experimentally matched to the respective cell or tissue type.

In addition to the composition of the cryomedium, the freezing and thawing profile (rate, temperature gradients, duration etc.) have an essential role for the preservation of high cell vitalities. Numerous protocols for various types of samples and preservation conditions have been published which describe both fast and slow cooling and thawing rates or a combination of the two (see, for example, J. M. Baust et al. in "Cell Transplantation", vol. 10, 2001, p. 561-571, and M. Miyamoto et al., in "Cell Transplantation" vol. 10, 2001, p. 363-371). It has been shown that a precisely controlled temperature regulation is required in each case since the cell vitality depends very strongly on the cooling/thawing rate.

If cell suspensions or tissue are frozen in conventional plastic cryovessels, it is not guaranteed that the same cooling rate is precisely maintained over all cells in the sample. Contributory factors to this are on the one hand the unfavorable surface/volume ratio (cryovessel/cell sample) and on the other hand, the low thermal conductivities of the conventionally used plastic of the cryovessels and the aqueous cryomedium.

This not only results in a steep temperature gradient inside the frozen sample but also in a strong spatial inhomogeneity of the cooling rate. The individual cells experience different temperature conditions, cooling and thawing rates according to their position in the sample.

This strong inhomogeneity in the cooling rates for the individual cells thus results in severe losses in the vitality since only the provision of the optimal cooling rate at all cells results in a high vitality of the sample.

In order to avoid and eliminate these problems, the following solution attempts are known. When freezing pig sperm cells in flat plastic containers (so-called flat-packs), B. M. Eriksson et al. (see "Anim. Reprod. Sci." vol. 63, 2000, p. 205-220) were able to demonstrate a significant increase in the mobility of the sperm cells compared to freezing in cylindrical plastic tubes (so-called maxi-straws). The authors gave the reasons for this result as a more uniform freezing and thawing process in the flat cryovessels. Also problematical is a severely reduced thawing rate in the core of the samples in the "maxi-straws" as a result of the insulating properties of the already thawed water in the periphery of the samples.

S.-P. Park et al. (see "Human Reproduction" vol. 15, 2000, p. 1787-1790) describe the ultra-fast freezing of human embryos on copper lattices which were originally designed for electron microscopy. In this case, very rapid heat removal takes place when the samples are inserted in liquid nitrogen, which is again beneficial to the vitality of the embryos.

A commercially available system for the storage of microorganisms is known from practice (product "micrybank", manufacturer: SensLab-GmbH, Leipzig, Germany). Microorganisms are bound to the porous surface of ceramic spheres which are preserved in a special cryomedium. This system however merely serves for improved handling of the samples. The freezing process is not optimised. The ceramic spheres have a lower thermal conductivity so that rapid freezing or thawing is impeded. In addition, because of their size, cells or tissue are not suited for adsorption on the porous surfaces.

It is also known to freeze biological samples in the form of very small sample volumes (ml or µl range) on suitably structured, two-dimensional cryosubstrates. In this case, said problems of temperature and cooling rate gradients are avoided. With this technique, only small quantities of samples can be stored on a cryosubstrate, which can be disadvantageous in applications requiring large sample volumes (e.g. in the ml range).

The object of the invention is to provide improved sample carriers for the cryopreservation of biological samples with which the disadvantages of conventional sample carriers are overcome. Sample carriers according to the invention should in particular make it possible to reproducibly set defined freezing or thawing protocols wherein temperature gradients or variations in the cooling or thawing rate inside a sample should be avoided. The sample carrier should furthermore be suitable for the preservation of large sample volumes. The object of the invention is also to provide improved methods for cryopreservation with which the disadvantages of conventional cooling or thawing protocols are avoided.

SUMMARY OF THE INVENTION

According to a first important aspect of the invention, a sample carrier is provided for the cryopreservation of especially biological samples with at least one sample reservoir for receiving a biological sample in which there is arranged a carrier body made of a material having a structure which has a plurality of internal, open cavities which can be filled with the sample. The carrier body with the internal cavities has an inner surface which is substantially greater than the inner surface of the sample reservoir. By this measure the surface/volume ratio is advantageously considerably improved compared with conventional sample carriers. By thermally conducting connection of the carrier body to a cooling medium, the cooling and thawing processes can be considerably homogenized in relation to the temperature distribution and the rate of the temperature change.

According to a preferred embodiment of the invention, the carrier body consists at least partly of a material which has a thermal conductivity like a metal. Thus, the actual temperature of the coolant can be transferred to the sample at an increased rate. Advantageously cooling and thawing protocols can be run through with higher accuracy and reproducibility. The carrier body preferably consists of a metal, a metal alloy or a composite material which contains a metal or a metal alloy. The carrier body can also consist of a polymer or ceramic material whose inner surface is coated with a metal, a metal alloy, a semiconductor material or a chemical compound which has a thermal conductivity corresponding to the thermal conductivity of metals. The polymer can, for example, be formed by a synthetic plastic or a solid material based on a natural organic material, especially cellulose-based, such as formed by pyrolised wood for example.

The structure with internal cavities is preferably formed by a body whose volume is permeated with honeycombs, pores, channels or other permeable structures. The smallest cross-sectional dimension of the cavities is advantageously in the range of 1 µm to 10 mm, preferably in the range of 5 µm to 5 mm. The cavities can be arranged regularly (honeycomb structure) or irregularly (internally coated, plant or animal tissue or organs, sponge or foam structure). The regular arrangement has the advantage that the sample volume received in the carrier body can be specified quantitatively more accurately. The irregular structure can generally be manufactured with a more favorable surface/volume ratio depending on the method of manufacturing the carrier body.

The carrier body with the internal surface is preferably matched in its external shape to the inner shape of the at least one sample reservoir of the sample carrier according to the invention. This feature has the advantage of a high utilisation of the sample reservoir volume and homogenization of the cryopreservation conditions in the entire sample reservoir. The carrier body can be arranged fixedly or detachably in the sample reservoir. Fixed attachment has the advantage that the sample carrier according to the invention forms a compact, independent component which is especially easy to handle in automated systems. If the carrier body is removable from the sample reservoir, there are advantages in relation to cleaning and/or pre-treatment of the carrier body (e.g. pre-cooling).

A further advantage of the invention is that the carrier body can be used as a heat exchanger. For example, if the sample reservoir is only partly filled so that only part of the hollow structure of the carrier body contains a sample, the remaining overlying structure can be used for heat exchange. For example, a vaporous coolant can extend over the free parts of the carrier body and thereby accelerate the heat removal. Conversely, it is possible to speed up the heat supply during thawing. According to an advantageous embodiment the carrier body can additionally be equipped with a heat exchange element which is protrudes from the carrier body and projects into the coolant. In this arrangement the heat exchange is improved when the carrier body is completely filled.

According to an advantageous embodiment of the invention, the carrier body is formed from the carrier material of a conventional catalyst, such as that used in motor vehicles to reduce pollutants. Carrier bodies comprising catalyst structures consist, for example, of a steel or ceramic base material coated with a precious metal (e.g. platinum). The use of catalyst structures has the particular advantage that the known catalyst carriers are already optimised in relation to their large inner surface and consist of inert materials suitable for use in cryopreservation.

According to a further advantageous embodiment of the invention, the carrier body consists of a so-called biomorphous ceramic which is made of a polysaccharide-based material. This material can advantageously be made of plants. Depending on the growth properties of the plants, cavities can be adjusted with the respectively desired size parameters. Another advantage of biomorphous ceramics is their biocompatibility.

A subject of the invention is also a method for cryopreservation using said sample carrier. A biological sample is applied to the carrier body using inherently available techniques such as pipetting or decanting, for example, and is received by said carrier body. According to a preferred embodiment of the method according to the invention, a pre-cooled carrier body is used. Advantageously, the sample is thus subjected to a uniform pre-cooling before the actual cooling process.

Biological samples preserved according to the invention generally comprise liquids containing biological material. The liquid for example, comprises a culture medium, a nutrient solution or another compatible enveloping medium. The invention can advantageously be used for biological materials of interest, such as for example, cells, cell groups, natural or artificial tissue, tissue pieces, organs, organ parts or cells of embryonic organisms. The sample is present for example as a suspension sample or as liquid in which the biological material is incorporated. The sample can thus also comprise liquids in which biological materials lie on the bottom of the vessel for example. The dimensions of the materials and the cavities in the sample carrier are generally matched to one another. Biological tissue or tissue parts provided for tissue production ("tissue engineering") can advantageously be preserved.

BRIEF DESCRIPTION OF SEVERAL VIEWS OF THE DRAWINGS

Further advantages and details of the invention are described in the following with reference to the appended drawings. In the figures.

DETAILED DESCRIPTION OF PREFERRED EMODIMENTS OF THE INVENTION

Figure 1:
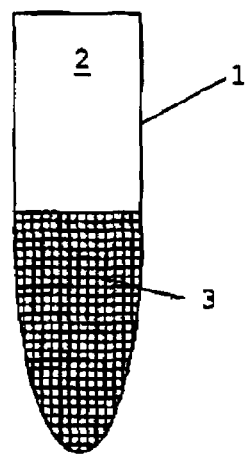
FIGS. 1 and 2: show schematic views of various embodiments of the sample carrier according to the invention.

A sample carrier 1 according to the invention in accordance with the embodiment illustrated in FIG. 1 comprises a sample reservoir 2 in which a carrier body 3 is arranged.

The sample carrier 1 has the shape, for example, of a cylinder closed at the bottom. It can for example, be formed by an inherently known sample tube or test tube. The carrier body 3 has a volume structure with a large inner surface. The outer shape of the carrier body 3 is matched to the inner shape of the sample reservoir or is formed slightly larger (see below). The internal volume of the sample reservoir 2 taken up by the carrier body 3 is for example in the range of 0.5 to 10 ml, preferably 1 to 5 ml.

The carrier body 3 consists, for example, of a porous, honeycomb-like, sponge- or foam-like metal material with a high thermal conductivity or of internally coated plant or animal tissue or organs. The carrier body advantageously makes it possible to achieve a specific, fast and controllable supply and removal of heat. The thermal conductivity is, for example, at least 0.1 J/K kg. The ratio of the inner surface to the volume of the carrier body depends on the type of carrier body material used and/or its conditions of manufacture. In the specific application the carrier body material or said surface-volume ratio is selected according to the properties of the samples to be preserved (e.g. suspension samples) and the available cryoinstallation. The ratio can for example be 4000 $m^{-1}$. The internal cavities of the carrier body are bounded by walls whose thickness is preferably less than 0.2 to 0.5 mm.

The carrier body 3 is, for example, formed of the material of a metal catalyst for a motor vehicle. The pore size or number of cells per volume is selected depending on the application according to the biological samples to be preserved. The carrier body 3 consists for example of platinum (thermal conductivity 0.032 J/K kg), steel (0.11 J/K kg) or aluminium (0.22 J/K kg). The carrier body 3 is for example cut to size from a metal or ceramic metal catalyst for motor vehicles from the manufacturer Matrix, Fürstenfeldbruck, Germany.

An advantage of the conventional catalyst structures is their low thermal expansion. In the various phases of a preservation process, the carrier body substantially retains its outer dimensions.

Alternatively, the carrier body can consist of a composite material of a polymer or ceramic with an inner coating of a good heat-conducting material. The carrier material can furthermore be manufactured from a natural polysaccharide-based material (e.g., cellulose, alginate, pectins), especially based on wood or plant fibres, which has been subjected to pyrolisation and treatment of the inner surface e.g. by silanisation or metal deposition (so-called biomorphous ceramic). Silanised wood with a porous structure is especially suited as carrier body as is described in P. Greil in "Journal of the European Ceramic Society", vol. 21, 2001, p. 105-188. Further examples of biocompatible materials of plant or animal origin comprise carrier bodies based on cacti, euphorbias, diatoms, papyrus reeds, algae, hollyhocks, elder, imprinted animal skins, bones, especially tubular bones, sponges and honeycombs. Alternatively, the carrier body can be made from a natural, porous mineral, e.g. expanded clay, with an inner coating.

A carrier body made of biomorphous ceramic is manufactured by the following method. Firstly, a wooden body is pyrolysed to form a corresponding guiding bundle framework made of carbon. Pyrolisation takes place for example at 1400° C. The guiding bundle framework is then dipped in a coating bath. The liquid of the coating bath wets the inner surface of the guiding bundle framework. The coating takes place, for example, in a silicon melt at around 1600° C. During cooling of the framework body removed from the melt, a silicon layer is deposited on the inner surface. Carrier bodies with various pore sizes can advantageously be produced depending on the choice of wood used. Furthermore, there is a large variability in relation to the outer dimensions of the carrier body. Silanised bamboo for example yields carrier bodies having diameters of around 1 to 5 cm. Carrier bodies with diameters up to around 1 cm can be produced using rattan.

Alternatively to silanisation, the pyrolised conducting bundle framework (xylem) can be coated with biocompatible, non-toxic metals. A gold or platinum melt, for example, can be used as a coating bath.

The inner surface of a carrier body can generally have a multiple coating. For example, in the case of biomorphous ceramics a multiple layer of silicon, gold and other biocompatible materials can be formed. In general, techniques such as those known from the semiconductor technology of wafer coating can be used for coating inner surfaces of carrier bodies.

A further advantage of carrier bodies is their mechanical deformability. Although the carrier bodies inherently consist of a solid material, their outer shape is easily elastically deformable because of the highly permeable volume structure. The carrier body can initially be manufactured with an outer shape slightly larger than the inner shape of the sample reservoir. When the carrier body is inserted into the sample reservoir, this is compressed so that it fits tightly in the sample reservoir under the action of the elastic deformation.

Figure 2:
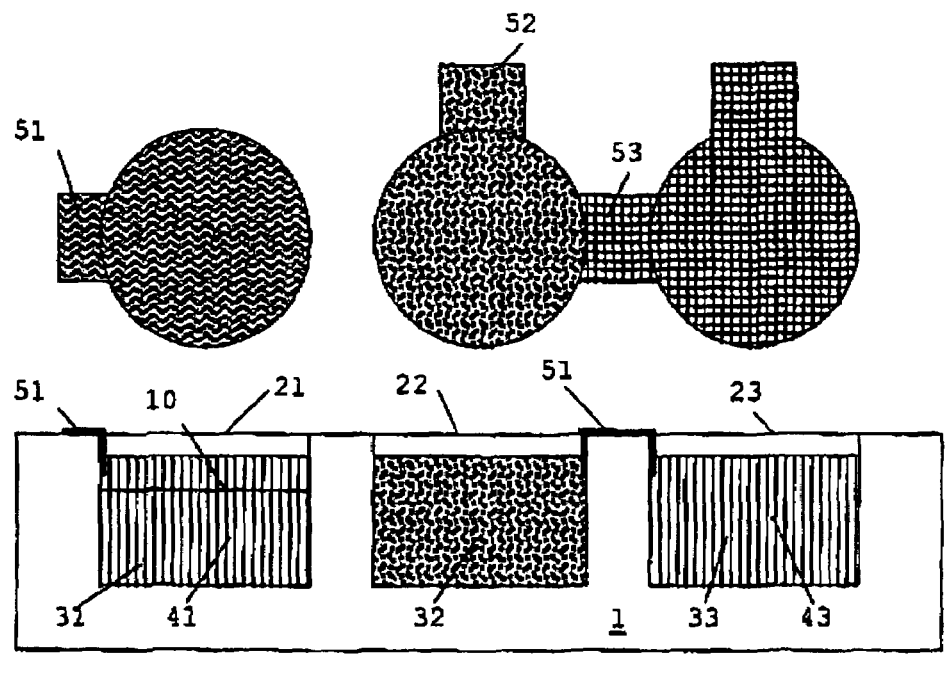

FIG. 2 illustrates a sample carrier 1 in the form of a cell culture plate with a plurality of sample reservoirs 21, 22, 23, . . . , in which respectively one carrier body 31, 32, 33, . . . is arranged. The sample reservoirs have a cylindrical shape for example. In the upper part of FIG. 2, the carrier bodies are illustrated schematically in plan view. The different patterns of the part diagrams A, B and C illustrate the different forms of internal cavities with which a carrier body according to the invention can be equipped.

For example, the carrier body according to FIG. 2A consists of corrugated sheets which are joined together offset or using interposed flat surfaces such that a plurality of straight channels 41 are formed. The channels 41 permeate the carrier body in the axial direction. According to FIG. 2B, the carrier body has a disordered honeycomb structure. FIG. 2C shows an ordered honeycomb structure, also with axially running channels 43.

FIG. 2A schematically illustrates the filling height of a suspension sample 10. The exposed region of the carrier body 31 above the filling height promotes heat exchange with the surroundings. In order to further improve the heat exchange even when the carrier body is completely filled, this can be equipped with at least one projecting heat exchange element 51. The heat exchange element 51 consists, for example, of the same material as the carrier body. For example, there is provided a projecting strip which projects into the space or is arranged on the surface of the wall of the sample reservoir.

Heat exchange elements 52, 53 can also be provided as connections between carrier bodies of adjacent sample reservoirs, as is illustrated schematically in FIGS. 2B and 2C. A composite structure is formed from a plurality of carrier bodies 32, 33 using the heat-exchange elements 52, 53, with which a plurality of sample reservoirs can be equipped simultaneously. According to the invention carrier bodies which are arranged, for example, according to the format of a micro- or nanotitre plate and are interconnected by means of heat-exchange elements, can form a carrier body composite structure.

For cryopreservation a sample carrier 1 according to FIG. 1 or FIG. 2 is brought into association with a coolant which is coupled to the carrier body in direct heat exchange or indirectly, mediated via the wall material of the sample reservoir and/or heat-exchange elements.

Exemplary Embodiment

Figure 3:
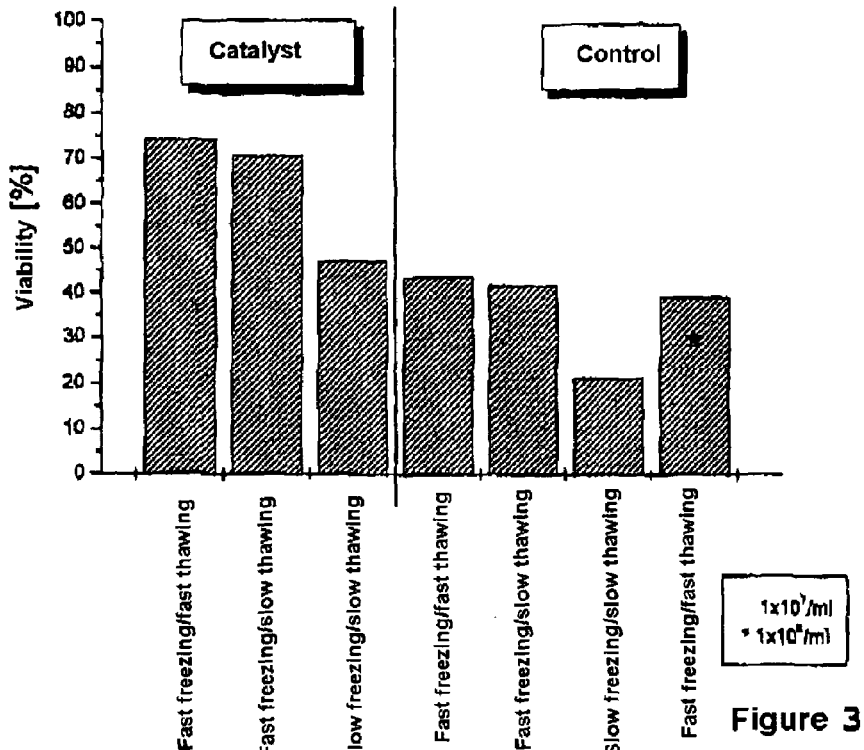
FIGS. 3 and 4: show experimental results which were achieved using the sample carrier according to the invention.
Figure 4:
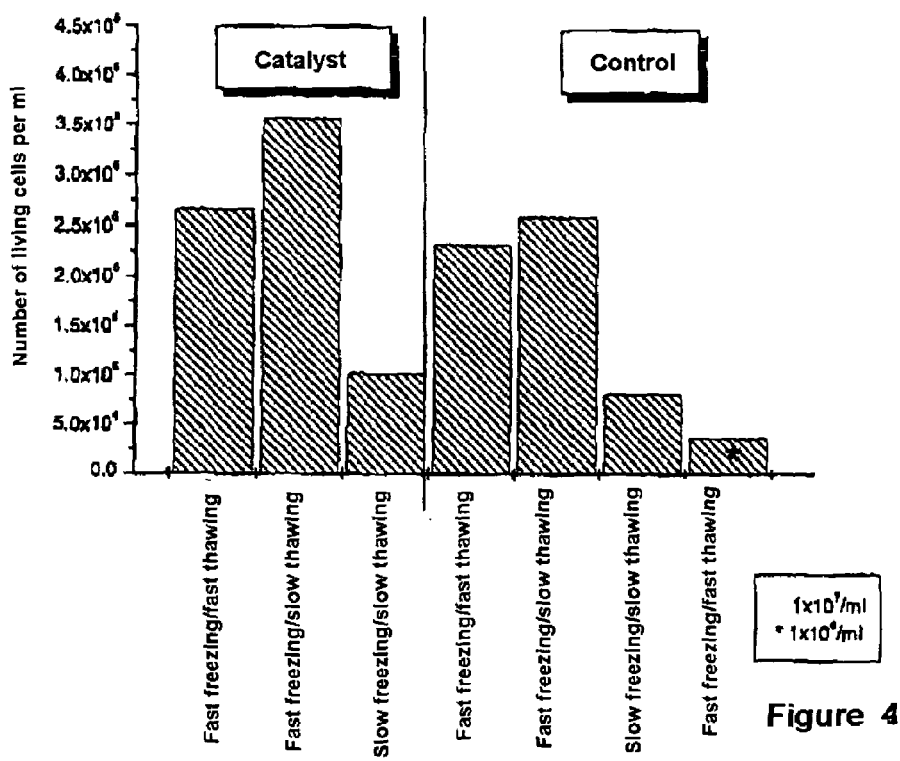

The test results illustrated in FIGS. 3 and 4 were determined under the following experimental conditions. Cells of the cell line Sp2 were cryopreserved from the exponential growth phase. A mixture of 90% FCS and 10% DMSO or a trehalose-containing solution was used as the cryomedium. A cell culture plate according to FIG. 2 with six sample reservoirs was used as the sample carrier. A disk of a catalyst material having a volume of around $0.5*2*2 cm^3$ was used in each sample reservoir. The carrier bodies were sterilized with ethanol and closed with a plastic layer on their underside.

In order to prepare a suspension sample Sp2 cells are first collected in culture bottles and analysed using a CASY measurement in relation to the size distribution and cell number. A suspension sample with $8.2*10^5$ cells per ml was formed. The suspension sample was centrifuged before the cryopreservation for about 10 minutes at 1000 rpm. The cell pellets formed were re-suspended in 1 ml of pre-cooled coolant and pipetted into the carrier body.

Various freezing and thawing protocols were implemented. Rapid freezing means immediate transfer to a −80° C. chest. Slow cooling means pre-cooling for one hour in a −20° C. chest, followed by transfer to a −80° C. chest. Rapid thawing means direct transfer from a −80° C. chest to room temperature. Slow thawing comprises first heating for one hour in a −20° C. chest, storage for 30 minutes on ice whilst pipetting 10 ml of CGM (37° C.) and repeated resuspension of the samples.

In order to check the cryopreservation result, the thawed samples were centrifuged and re-suspended in CGM. After culturing for 24 h at 37° C. and 5% $CO_2$, a CASY measurement was made to determine the cell number, the size distribution and the vitality of the cells after the cryopreservation. FIGS. 3 and 4 show the results for various freezing and thawing protocols using a sample carrier according to the invention compared with a control sample (cryopreservation in test tube). The cryopreservation according to the invention gives a considerable increase in the viability and number of living cells for all test conditions, especially the fast freezing processes.

The invention claimed is:

1. A sample carrier for cryopreservation of biological materials, comprising:
    at least one sample reservoir for receiving a biological sample for cryopreservation, and
    a carrier body being arranged in the at least one sample reservoir, being made of a material with a volume structure, and having a plurality of open, internal cavities adapted to hold the biological sample, wherein the material of the carrier body is made of an alginate.

2. The sample carrier according to claim 1, wherein the carrier body consists of a material whose thermal conductivity is identical to a thermal conductivity of metals.

3. The sample carrier according to claim 1, wherein the carrier body consists of a composite material wherein the internal cavities are at least partly coated with a material whose thermal conductivity is identical to a thermal conductivity of metals.

4. The sample carrier according to claim 1, wherein the carrier body has honeycombs, pores, channels or sponge- or foam-like cavities.

5. The sample carrier according to claim 1, wherein the shape of the carrier body is matched to an internal shape of the sample reservoir or is slightly larger.

6. The sample carrier according to claim 5, wherein the carrier body fits tightly in the sample reservoir under action of an elastic deformation.

7. The sample carrier according to claim 1, which is equipped with at least one heat-exchange element.

8. The sample carrier according to claim 7, wherein a plurality of sample reservoirs are provided and respectively relevant carrier bodies are interconnected via the at least one heat exchange element.

9. A method for cryopreservation of biological material, wherein biological samples are poured into a sample carrier according to claim 1, and the sample carrier is subjected to a cooling process.

10. The method according to claim 9, wherein a pre-cooled carrier body is used.

11. A method of producing the sample carrier of claim 1, said method comprising providing an alginate as the carrier body for receiving samples for cryopreservation.

* * * * *